US012048680B2

(12) United States Patent
Yao et al.

(10) Patent No.: US 12,048,680 B2
(45) Date of Patent: Jul. 30, 2024

(54) USE OF GEMFIBROZIL AND DERIVATIVE THEREOF FOR TREATMENT AND/OR PREVENTION OF NEURODEGENERATIVE DISEASE

(71) Applicant: Kunming Institute of Zoology Chinese Academy of Sciences, Kunming (CN)

(72) Inventors: Yonggang Yao, Kunming (CN); Rongcan Luo, Kunming (CN); Guiyu Li, Kunming (CN); Lingyan Su, Kunming (CN); Jing Yang, Kunming (CN); Dengfeng Zhang, Kunming (CN)

(73) Assignee: KUNMING INSTITUTE OF ZOOLOGY CHINESE ACADEMY OF SCIENCES, Yunnan (CN)

( * ) Notice: Subject to any disclaimer, the term of this patent is extended or adjusted under 35 U.S.C. 154(b) by 679 days.

(21) Appl. No.: 17/278,994

(22) PCT Filed: Sep. 18, 2019

(86) PCT No.: PCT/CN2019/106476
§ 371 (c)(1),
(2) Date: Mar. 23, 2021

(87) PCT Pub. No.: WO2020/082941
PCT Pub. Date: Apr. 30, 2020

(65) Prior Publication Data
US 2022/0031643 A1    Feb. 3, 2022

(30) Foreign Application Priority Data
Oct. 24, 2018 (CN) .......................... 201811241909.0

(51) Int. Cl.
*A61K 31/192* (2006.01)
*A61K 31/13* (2006.01)
(Continued)

(52) U.S. Cl.
CPC ............ *A61K 31/192* (2013.01); *A61K 31/13* (2013.01); *A61K 31/24* (2013.01); *A61K 31/445* (2013.01);
(Continued)

(58) Field of Classification Search
CPC .. A61K 31/192; A61K 31/196; A61K 31/216; A61P 25/16; A61P 25/28; A61P 25/14
See application file for complete search history.

(56) References Cited

U.S. PATENT DOCUMENTS

2012/0058992 A1   3/2012   Cohen et al.
2019/0125743 A1   5/2019   Nirogi et al.

FOREIGN PATENT DOCUMENTS

CN       102065898 B    8/2015
WO    WO-2011/153247 A1  12/2011
(Continued)

*Primary Examiner* — Deborah D Carr
(74) *Attorney, Agent, or Firm* — Muncy, Geissler, Olds & Lowe, P.C.

(57) ABSTRACT

A use of Gemifibrozil and a pharmaceutically acceptable salt, ester, or stereoisomer thereof in the preparation of a medicament for the treatment and/or prevention of a neurodegenerative disease. The neurodegenerative disease is selected from Alzheimer's disease, Parkinson's disease, Huntington's disease, or amyotrophic lateral sclerosis. Further provided is a pharmaceutical composition for treating and/or preventing a neurodegenerative disease, wherein the pharmaceutical composition comprises Gemifibrozil, or a pharmaceutically acceptable salt, ester, or stereoisomer thereof, and, preferably, the pharmaceutical composition further comprises one or a plurality of pharmaceutically acceptable carriers. Further provided is a use of the pharmaceutical composition comprising Gemifibrozil, or a pharmaceutically acceptable salt, ester, or stereoisomer thereof in the preparation of a medicament for the treatment and/or prevention of a neurodegenerative disease.

7 Claims, 6 Drawing Sheets

(51) Int. Cl.
*A61K 31/24* (2006.01)
*A61K 31/445* (2006.01)
*A61K 31/55* (2006.01)
*A61K 31/702* (2006.01)
*A61P 25/16* (2006.01)
*A61P 25/28* (2006.01)

(52) U.S. Cl.
CPC ............ *A61K 31/55* (2013.01); *A61K 31/702* (2013.01); *A61P 25/16* (2018.01); *A61P 25/28* (2018.01)

(56) References Cited

FOREIGN PATENT DOCUMENTS

| WO | WO-2016/201086 A1 | 12/2016 | | |
|---|---|---|---|---|
| WO | WO-2017/160629 A1 | 9/2017 | | |
| WO | WO-2017/199071 A1 | 11/2017 | | |
| WO | WO-2017199071 A1 * | 11/2017 | ............. | A61K 31/27 |
| WO | WO-2018/126000 A1 | 7/2018 | | |
| WO | WO-2018126000 A1 * | 7/2018 | ........... | A61K 31/192 |

\* cited by examiner

USE OF GEMFIBROZIL AND DERIVATIVE THEREOF FOR TREATMENT AND/OR PREVENTION OF NEURODEGENERATIVE DISEASE

This application claims priority to Chinese Patent Application No. 201811241909.0, entitled "Use of Gemfibrozil and derivative thereof for the treatment and/or prevention of neurodegenerative disease", filed to the Chinese Patent Office on Oct. 24, 2018, the entire contents of which are incorporated herein by reference.

TECHNICAL FIELD

This application relates to the technical field of new use of medicaments, in particular to use of Gemfibrozil and derivative thereof in the preparation of medicaments for the treatment and/or prevention of the neurodegenerative disease.

BACKGROUND ART

Gemfibrozil, chemical name: 2, 2-dimethyl-5-(2, 5-dimethylphenoxy) pentanoic acid, has the following structural formula:

Gemfibrozil, known as a clofibric acid derivative blood lipid regulating drug, is used for treating hyperlipidemia, and is suitable for patients with severe type IV or V hyperlipoproteinemia, coronary heart disease, type IIb hyperlipoproteinemia and other subjects who have failed to treat blood lipids by drugs.

Neurodegenerative diseases (NDD), including Alzheimer's disease (AD), Parkinson's disease (PD), amyotrophic lateral sclerosis (ALS) and Huntington's disease (HD), are very harmful brain lesions, and have gradually become a worldwide health care problem. Unfortunately, for these diseases, treatment regimens remain limited in the control of the condition and there are no modified medicaments that can prevent the disease from occurring. Although these diseases have their own characteristics, in many cases they will have some of the same symptoms and neuropathological conditions.

For example, Alzheimer's disease (AD), commonly known as senile dementia, is the most common neurodegenerative disease in the world. With the rapid aging of the population, its incidence is increasing. The clinical manifestations comprise continued deterioration of cognitive and memory function, progressive decline of daily living ability, accompanied by various neuropsychiatric symptoms and behavior disorders. The common early symptoms comprise mild cognitive impairment, difficulty in remembering recent events, accompanied by apathy and depression. As the disease progresses, the symptoms may develop into the loss of long-term memory, the inability to correctly recognize and judge the surrounding things, and even the inability to recognize relatives. In addition, there will be loss of language ability and behavior disorders, inability to complete simple actions such as walking and swallowing, complete loss of communication and self-care ability, and the gradual loss of body functions, eventually leading to death. In China, about 10 million people are troubled by AD, ranking first in the world. About 5.5 million Americans have AD, and this number will reach 13.8 million by the middle of this century. In developed countries, AD is one of the main diseases that consume social financial subsidies.

AD is characterized by progressive memory loss and other cognitive disorders, such as impaired motor skills, impaired reasoning and judging ability. The main pathological features of AD include senile plaques formed by aggregation of β-amyloid (Aβ) outside the neurons, neurofibrillary tangles formed by aggregation of hyperphosphorylated microtubule-associated protein tau (MAPT) of in the neuron, and synaptic dysfunction and neuronal loss.

At present, the treatment of AD is mainly adjuvant therapy. These medicaments can only improve the patient's symptoms to a certain extent, and there is no medicament that can completely cure the disease.

The existing adjuvant therapy medicines are as follows:

Donepezil (Aricept®) was approved in the United States and the European Union in 1996 and 1997. The treatment mechanism is to inhibit acetylcholinesterase, thereby enhancing cholinergic transmission, which is lacking in AD patients.

Rivastigmine (Exelon®) was approved in the European Union and the United States in 1998 and 2000, respectively, and its mechanism of action is also to inhibit acetylcholinesterase.

Galantamine (Razadyne®) was approved in the European Union and the United States in 2000 and 2001, respectively, and its mechanism of action is very similar to Donepezil (Aricept®).

Memantine hydrochloride (Namenda®) was approved in the European Union and the United States in 2002 and 2003, respectively. It was the first drug to reduce excessive calcium influx and inhibit neurotoxicity and apoptosis by blocking N-methyl-D-aspartate receptors.

Sodium oligomannate (GGV-971®) is a marine oligosaccharide molecule extracted from seaweed, which can capture Aβ in multiple sites, fragments and states, inhibit the formation of Aβ fibrils, and depolymerize the formed fibrils into non-toxic monomers. Sodium oligomannate (GGV-971®) also regulates the imbalance of intestinal flora and remodels the body's immune homeostasis, thereby reducing neuroinflammation in the brain and preventing the progression of AD. This significant study further demonstrates that Aβ clearance plays a positive role in improving the onset of AD symptoms.

SUMMARY OF THE INVENTION

The inventors of the present application have unexpectedly found that Gemfibrozil is effective in ameliorating and/or treating neurodegenerative diseases, particularly AD, through intensive studies of Gemfibrozil, and have completed the present application based thereon. The specific technical solutions are as follows:

This application first provides use of Gemifibrozil and a pharmaceutically acceptable salt, ester, or stereoisomer thereof in the preparation of a medicament for the treatment and/or prevention of a neurodegenerative disease.

In some embodiments of the present application, Gemifibrozil and the pharmaceutically acceptable salt, ester, or stereoisomer thereof can treat and/or prevent the neurodegenerative disease by activating astrocytes and microglia to gather around Aβ to clear them.

In some embodiments of this application, the neurodegenerative diseases include but are not limited to Alzheimer's disease, Parkinson's disease, Huntington's disease, or amyotrophic lateral sclerosis.

In some embodiments of the present application, the daily dosage of the medicament administered to a subject in need thereof is 0.1-100 mg/kg body weight, preferably 0.5-20 mg/kg body weight, based on Gemfibrozil, the pharmaceutically acceptable salt, ester, or stereoisomer thereof.

Further provided is a pharmaceutical composition for treating and/or preventing a neurodegenerative disease, wherein the pharmaceutical composition comprises Gemifibrozil, or a pharmaceutically acceptable salt, ester, or stereoisomer thereof.

In some embodiments of the present application, the pharmaceutical composition further comprises one or more pharmaceutical carriers.

In some embodiments of the present application, Gemifibrozil and the pharmaceutically acceptable salt, or stereoisomer thereof is present in a content of 1-99%, preferably 20-80%, more preferably 40-60%, based on the total weight of the pharmaceutical composition.

In some embodiments of the present application, the pharmaceutical composition further comprises a second therapeutically active agent.

In some embodiments of the present application, the second therapeutically active agent is selected from one or more of Donepezil (Aricept®), Rivastigmine (Exelon®) Galantamine (Razadyne®), Memantine hydrochloride (Namenda®), and sodium oligomannate (GGV-971®).

In some embodiments of the present application, the daily dosage of the pharmaceutical composition administered to a subject in need thereof is 0.1-100 mg/kg body weight, preferably 0.5-20 mg/kg body weight, based on Gemfibrozil, the pharmaceutically acceptable salt, ester, or stereoisomer thereof.

Further provided is use of the pharmaceutical composition comprising Gemifibrozil, or a pharmaceutically acceptable salt, ester, or stereoisomer thereof in the preparation of a medicament for the treatment and/or prevention of a neurodegenerative disease; preferably, the pharmaceutical further comprises one or more pharmaceutical carriers.

In some embodiments of the application, the pharmaceutical composition further comprises a second therapeutically active agent; preferably, the second therapeutically active agent is selected from one or more of Donepezil (Aricept®), Rivastigmine (Exelon®), Galantamine (Razadyne®), Memantine hydrochloride (Namenda®), and Sodium oligomannate (GGV-971®).

In some embodiments of the present application, the daily dosage of the pharmaceutical composition administered to a subject in need thereof is 0.1-100 mg/kg body weight, preferably 0.5-20 mg/kg body weight, based on Gemfibrozil, the pharmaceutically acceptable salt, ester, or stereoisomer thereof.

Further provided is use of the aforementioned Gemfibrozil, the pharmaceutically acceptable salt, ester, or stereoisomer thereof, or the aforementioned pharmaceutical composition in the treatment and/or prevention of a neurodegenerative disease.

Further provided is a method for treating and/or preventing neurodegenerative diseases, which includes administering to a patient in need a therapeutically effective amount of the aforementioned Gemfibrozil, a pharmaceutically acceptable salt, ester, or stereoisomer thereof, or the aforementioned pharmaceutical composition.

Clofibrate, chemical name: ethyl 2-methyl-2-(4-chlorophenoxy) propanoate, has the formula of:

Further provided is use of Clofibrate and a pharmaceutically acceptable salt, ester, or stereoisomer thereof in the preparation of a medicament for the treatment and/or prevention of a neurodegenerative disease.

In some embodiments of the present application, Clofibrate and the pharmaceutically acceptable salt, ester, or stereoisomer thereof can treat and/or prevent the neurodegenerative disease by activating astrocytes and microglia to gather around Aβ to clear them.

In some embodiments of this application, the neurodegenerative diseases include but are not limited to Alzheimer's disease, Parkinson's disease, Huntington's disease, or amyotrophic lateral sclerosis.

In some embodiments of the present application, the daily dosage of the medicament administered to a subject in need thereof is 0.1-100 mg/kg body weight, preferably 0.5-20 mg/kg body weight, based on Clofibrate, the pharmaceutically acceptable salt, ester, or stereoisomer thereof.

Further provided is a pharmaceutical composition for treating and/or preventing a neurodegenerative disease, wherein the pharmaceutical composition comprises the Clofibrate, or a pharmaceutically acceptable salt, ester, or stereoisomer thereof.

In some embodiments of the present application, the pharmaceutical composition further comprises one or more pharmaceutical carriers.

In some embodiments of the present application, Clofibrate, a pharmaceutically acceptable salt, ester, or stereoisomer thereof is present in a content of 1-99%, preferably 20-80%, more preferably 40-60%, based on the total weight of the pharmaceutical composition.

In some embodiments of the present application, the pharmaceutical composition further comprises a second therapeutically active agent.

In some embodiments of the present application, the second therapeutically active agent is selected from one or more of Donepezil (Aricept®), Rivastigmine (Exelon®), Galantamine (Razadyne®), Memantine hydrochloride (Namenda®), and Sodium oligomannate (GGV-971®).

In some embodiments of the present application, the daily dosage of the pharmaceutical composition administered to a subject in need thereof is 0.1-100 mg/kg body weight, preferably 0.5-20 mg/kg body weight, based on Clofibrate, the pharmaceutically acceptable salt, ester, or stereoisomer thereof.

Further provided is use of the pharmaceutical composition comprising Clofibrate, or a pharmaceutically acceptable salt, ester, or stereoisomer thereof in the preparation of a medicament for the treatment and/or prevention of a neurodegenerative disease; preferably, the pharmaceutical composition further comprises one or more pharmaceutical carriers.

In some embodiments of the application, the pharmaceutical composition further comprises a second therapeutically active agent; preferably, the second therapeutically active agent is selected from one or more of Donepezil (Aricept®), Rivastigmine (Exelon®) Galantamine (Razadyne®), Memantine hydrochloride (Namenda®), and Sodium oligomannate (GGV-971®).

In some embodiments of the present application, the daily dosage of the pharmaceutical composition administered to a subject in need thereof is 0.1-100 mg/kg body weight, preferably 0.5-20 mg/kg body weight, based on Clofibrate, the pharmaceutically acceptable salt, ester, or stereoisomer thereof.

Further provided is use of the aforementioned Clofibrate, the pharmaceutically acceptable salt, ester, or stereoisomer thereof, and the aforementioned pharmaceutical composition in the treatment and/or prevention of a neurodegenerative disease.

Further provided is a method for treating and/or preventing neurodegenerative diseases, which comprises administering to a patient in need a therapeutically effective amount of the aforementioned Clofibrate, a pharmaceutically acceptable salt, ester, or stereoisomer thereof, and the aforementioned pharmaceutical composition.

Fenofibrate, chemical name: isopropyl 2-methyl-2-[4 (4-chlorobenzoyl) phenoxy] propanoate, has the formula of:

Further provided is use of Fenofibrate and a pharmaceutically acceptable salt, ester, or stereoisomer thereof in the preparation of a medicament for the treatment and/or prevention of a neurodegenerative disease.

In some embodiments of the present application, Fenofibrate and the pharmaceutically acceptable salt, ester, or stereoisomer thereof can treat and/or prevent the neurodegenerative disease by activating astrocytes and microglia to gather around Aβ to clear them.

In some embodiments of this application, the neurodegenerative diseases include but are not limited to Alzheimer's disease, Parkinson's disease, Huntington's disease, or amyotrophic lateral sclerosis.

In some embodiments of the present application, the daily dosage of the medicament administered to a subject in need thereof is 0.1-100 mg/kg body weight, preferably 0.5-20 mg/kg body weight, based on Fenofibrate, the pharmaceutically acceptable salt, ester, or stereoisomer thereof.

Further provided is a pharmaceutical composition for treating and/or preventing a neurodegenerative disease, wherein the pharmaceutical composition comprises the Fenofibrate, or a pharmaceutically acceptable salt, ester, or stereoisomer thereof.

In some embodiments of the present application, the pharmaceutical composition further comprises one or more pharmaceutical carriers.

In some embodiments of the present application, Fenofibrate, a pharmaceutically acceptable salt, ester, or stereoisomer thereof is present in a content of 1-99%, preferably 20-80%, more preferably 40-60%, based on the total weight of the pharmaceutical composition.

In some embodiments of the present application, the pharmaceutical composition further comprises a second therapeutically active agent.

In some embodiments of the present application, the second therapeutically active agent is selected from one or more of Donepezil (Aricept®), Rivastigmine (Exelon®), Galantamine (Razadyne®), Memantine hydrochloride (Namenda), and Sodium oligomannate (GGV-971®).

In some embodiments of the present application, the daily dosage of the pharmaceutical composition administered to a subject in need thereof is 0.1-100 mg/kg body weight, preferably 0.5-20 mg/kg body weight, based on Fenofibrate, the pharmaceutically acceptable salt, ester, or stereoisomer thereof.

Further provided is use of the pharmaceutical composition comprising Fenofibrate, or a pharmaceutically acceptable salt, ester, or stereoisomer thereof in the preparation of a medicament for the treatment and/or prevention of a neurodegenerative disease; preferably, the pharmaceutical composition further comprises one or more pharmaceutical carriers.

In some embodiments of the application, the pharmaceutical composition further comprises a second therapeutically active agent; preferably, the second therapeutically active agent is selected from one or more of Donepezil (Aricept®), Rivastigmine (Exelon®), Galantamine (Razadyne®), Memantine hydrochloride (Namenda®), and Sodium oligomannate (GGV-971®).

In some embodiments of the present application, the daily dosage of the pharmaceutical composition administered to a subject in need thereof is 0.1-100 mg/kg body weight, preferably 0.5-20 mg/kg body weight, based on Fenofibrate, the pharmaceutically acceptable salt, ester, or stereoisomer thereof.

Further provided is use of the aforementioned Fenofibrate, the pharmaceutically acceptable salt, ester, or stereoisomer thereof, and the aforementioned pharmaceutical composition in the treatment and/or prevention of a neurodegenerative disease.

Further provided is a method for treating and/or preventing neurodegenerative diseases, which comprises administering to a patient in need a therapeutically effective amount of the aforementioned Fenofibrate, a pharmaceutically acceptable salt, ester, or stereoisomer thereof, and the aforementioned pharmaceutical composition.

Compound GW7647, chemical name: 2-((4-(2-(3-cyclohexyl-1-(4-cyclohexylbutyl) ureido) ethyl) phenyl) thio)-2-methylpropanoic acid, has the formula of:

Further provided is use of Compound GW7647 and a pharmaceutically acceptable salt, ester, or stereoisomer thereof in the preparation of a medicament for the treatment and/or prevention of a neurodegenerative disease.

In some embodiments of the present application, Compound GW7647 and the pharmaceutically acceptable salt, ester, or stereoisomer thereof can treat and/or prevent the neurodegenerative disease by activating astrocytes and microglia to gather around Aβ to clear them.

In some embodiments of this application, the neurodegenerative diseases include but are not limited to Alzheimer's disease, Parkinson's disease, Huntington's disease, or amyotrophic lateral sclerosis.

In some embodiments of the present application, the daily dosage of the medicament administered to a subject in need thereof is 0.1-100 mg/kg body weight, preferably 0.5-20 mg/kg body weight, based on Compound GW7647, the pharmaceutically acceptable salt, ester, or stereoisomer thereof.

Further provided is a pharmaceutical composition for treating and/or preventing a neurodegenerative disease, wherein the pharmaceutical composition comprises the aforementioned Compound GW7647, or a pharmaceutically acceptable salt, ester, or stereoisomer thereof.

In some embodiments of the present application, the pharmaceutical composition further comprises one or more pharmaceutical carriers.

In some embodiments of the present application, Compound GW7647, a pharmaceutically acceptable salt, ester, or stereoisomer thereof is present in a content of 1-99%, preferably 20-80%, more preferably 40-60%, based on the total weight of the pharmaceutical composition.

In some embodiments of the present application, the pharmaceutical composition further comprises a second therapeutically active agent.

In some embodiments of the present application, the second therapeutically active agent is selected from one or more of Donepezil (Aricept®), Rivastigmine (Exelon®), Galantamine (Razadyne®), Memantine hydrochloride (Namenda®), and Sodium oligomannate (GGV-971®).

In some embodiments of the present application, the daily dosage of the pharmaceutical composition administered to a subject in need thereof is 0.1-100 mg/kg body weight, preferably 0.5-20 mg/kg body weight, based on Compound GW7647, the pharmaceutically acceptable salt, ester, or stereoisomer thereof.

Further provided is use of the pharmaceutical composition comprising Compound GW7647, or a pharmaceutically acceptable salt, ester, or stereoisomer thereof in the preparation of a medicament for the treatment and/or prevention of a neurodegenerative disease; preferably, the pharmaceutical composition further comprises one or more pharmaceutical carriers.

In some embodiments of the application, the pharmaceutical composition further comprises a second therapeutically active agent; preferably, the second therapeutically active agent is selected from one or more of Donepezil (Aricept®), Rivastigmine (Exelon®), Galantamine (Razadyne®), Memantine hydrochloride (Namenda®), and Sodium oligomannate (GGV-971®).

In some embodiments of the present application, the daily dosage of the pharmaceutical composition administered to a subject in need thereof is 0.1-100 mg/kg body weight, preferably 0.5-20 mg/kg body weight, based on Compound GW7647, the pharmaceutically acceptable salt, ester, or stereoisomer thereof.

Further provided is use of the aforementioned Compound GW7647, the pharmaceutically acceptable salt, ester, or stereoisomer thereof, and the aforementioned pharmaceutical composition in the treatment and/or prevention of a neurodegenerative disease.

Further provided is a method for treating and/or preventing neurodegenerative diseases, which comprises administering to a patient in need a therapeutically effective amount of the aforementioned Compound GW7647, a pharmaceutically acceptable salt, ester, or stereoisomer thereof, and the aforementioned pharmaceutical composition.

As used herein, a "pharmaceutically acceptable salt" refers to a pharmaceutical acid and base addition salt or solvate thereof. Such pharmaceutically acceptable salts include salts of acids such as: hydrochloric acid, phosphoric acid, hydrobromic acid, sulfuric acid, sulfurous acid, formic acid, toluenesulfonic acid, methanesulfonic acid, nitric acid, benzoic acid, citric acid, tartaric acid, maleic acid, hydroiodic acid, and alkanoic acids such as acetic acid, HOOC—$(CH_2)$n-COOH where n is 0-4; and salts of bases: sodium salt, potassium salt, calcium salt, ammonium salt and the like. Those skilled in the art know a variety of non-toxic pharmaceutically acceptable addition salts.

As used herein, an "ester" refers to an ester that retains pharmaceutical activity and the properties of the parent compound, and includes, for example, pharmaceutical alkyl esters such as methyl, ethyl, isopropyl, butyl, sec-butyl, tert-butyl, pentyl, hexyl, cyclopentyl, cyclohexyl, and the like, or aromatic esters such as phenyl, naphthyl, benzyl, and phenethyl.

As used herein, a "stereoisomer" refers to that when a compound has asymmetric carbon atoms, it will produce an enantiomer; when a compound has a carbon-carbon double bond or a cyclic structure, it will produce cis-trans isomer; when a compound has a ketone or oxime, it will produce a tautomers. All enantiomers, diastereomers, racemic isomers, cis-trans isomers, tautomers, geometric isomers, epimers, and mixtures thereof are included within the scope of this application.

As used herein, a "pharmaceutical composition" can be a "therapeutically effective amount" of the afore mentioned Gemfibrozil, Clofibrate, Fenofibrate, GW7647, and the like, pharmaceutically acceptable salts, esters, or stereoisomers thereof, are administered in combination with one or more second therapeutically active agents, for example, sequentially, or simultaneously; or the therapeutically active ingredients are prepared into a compound preparation for administration.

As used herein, the frequency of administration of the "medicament" or "pharmaceutical composition" may be once a day or once a week or once, twice, three or more times a month, as needed to effectively treat the condition. Alternatively, the frequency of administration may be at least once every three months, as needed to effectively treat the condition. For example, it can be administrated about every 5 weeks, about every 6 weeks, about every 7 weeks, about every 8 weeks, about every 9 weeks, about every 10 weeks, about every 11 weeks, or about every 12 weeks. The frequency of administration may also vary depending on the therapeutically active ingredient employed and the particular condition being treated. However, for the treatment of most conditions, a dosing regimen of 4 times per day or less is preferred. It will be understood, however, that the specific dose level for any particular patient will depend upon a variety of factors including the activity of the therapeutically active ingredient employed, age, weight, general health, gender, diet, time of administration, route of administration, and rate of excretion, the pharmaceutical composition, and severity of the specific disease being treated.

As used herein, a "neurodegenerative disease" (NDD) is understood to be a disease caused by central nervous system hypofunction caused by progressive degenerative necrosis of nerve cells, including but not limited to Alzheimer's disease (AD), Parkinson's disease (PD), amyotrophic lateral sclerosis (ALS), Huntington's disease (HD), and the like.

"Treatment" as used herein has its general meaning, and specifically refers herein to the treatment on a mammalian individual, preferably a human, already suffering from a neurodegenerative disease as described herein, with a medicament of the present application, in order to produce a therapeutic, curative, alleviative, palliative, etc. effect on the disease. Similarly, as used herein, the term "prevention" has its general meaning, and specifically refers herein to the treatment on a mammalian individual that may or may be at risk of developing a neurodegenerative disease as described herein, with a medicament of the present application, in order to produce a preventive, prophylactic, restrictive, blocking, etc. effect on the disease.

As used herein, a "pharmaceutical carrier" can be one or more solid or liquid fillers or gelling materials suitable for human use. The pharmaceutical carriers are preferably of sufficient purity and sufficiently low toxicity and are compatible with the active ingredients of the present application (Gemfibrozil, Clofibrate, Fenofibrate, GW7647, etc., pharmaceutically acceptable salts, esters, or stereoisomers thereof) and do not significantly reduce the efficacies of the active ingredients. For example, pharmaceutical carriers can be fillers, binders, disintegrants, lubricants, aqueous or non-aqueous solvents, and the like.

The pharmaceutical compositions described herein may be formulated in any pharmaceutically acceptable dosage form so as to be administrated to a patient or subject in need of such treatment in any suitable manner, e.g., by oral, parenteral, rectal or pulmonary administration. When used for oral administration, it can be made into tablets, capsules, pills, granules, etc. When used for parenteral administration, it can be made into injection, sterile powder for injection, etc.

As used herein, a "therapeutically effective amount" refers to an amount of the afore mentioned Gemfibrozil, Clofibrate, Fenofibrate, GW7647, etc., or pharmaceutically acceptable salts, esters, or stereoisomers thereof, as well as the afore mentioned pharmaceutical compositions that, when administered to a patient, can at least alleviate the symptoms of the patient's condition. The actual amount comprising a "therapeutically effective amount" will vary depending upon a variety of circumstances including, but not limited to, the particular condition being treated, the severity of the condition, the physical and health status of the patient, and the route of administration. A skilled medical practitioner can readily determine the appropriate amount using methods known in the medical arts.

This application unexpectedly discovered through experiments that gemfibrozil can effectively improve and/or treat AD. Therefore, Gemifibrozil and a pharmaceutically acceptable salt, ester, or stereoisomer thereof can be used in the preparation of a medicament for the treatment and/or prevention of a neurodegenerative disease. Further provided is Gemifibrozil and a pharmaceutically acceptable salt, ester, or stereoisomer thereof, which can also be used in the preparation of a medicament for the prevention and/or treatment of a neurodegenerative disease.

BRIEF DESCRIPTION OF THE DRAWINGS

In order to more clearly describe the technical solutions in the embodiments of the present application or the prior art, the drawings used in the description of the embodiments or prior art are briefly described below, and it is obvious that the drawings in the description below are only some embodiments of the present application, and that other drawings can be obtained from these drawings without involving any inventive effort for a person skilled in the art.

DETAILED DESCRIPTION OF THE INVENTION

The technical solutions in the embodiments of the present application will be described clearly and completely in conjunction with the accompanying drawings in the embodiments of the present application. Obviously, the described embodiments are only a part of the embodiments of the present application, rather than all the embodiments. Based on the embodiments of the present application, all other embodiments obtained by a person of ordinary skill in the art without involving any inventive effort are within the scope of the present application.

First, experimental materials, experimental methods and the like related to the present application are described.
Experimental Material Sources:

Gemfibrozil: purchased from Abcam Inc.

AD mice (APP/PS1ΔE9 mice) overexpressing human APP mutation (Swedish mutation) and PSEN1 (PS1) with the 9th exon deleted: purchased from Nanjing Biomedical Research Institute of Nanjing University (NBRI), and raised in Laboratory Animal Breeding Center, Kunming Institute of Zoology of Chinese Academy of Sciences. APP/PS1ΔE9 mice are available referring to the detailed description in Jankowsky et al. (2004) Mutant presenilins specifically elevate the levels of the 42 residue beta-amyloid peptide in vivo: evidence for augmentation of a 42-specific gamma secretase. Hum Mol Genet. 13(2):159-70.

All experimental animals were obtained from the Laboratory Animal Breeding Center, Kunming Institute of Zoology, CAS. The handling and experimental methods of the mice are in compliance with the requirements of the ethics committee of the Kunming Institute of Zoology, CAS. All animals were housed in an environment of 23-25° C. with a 12-hour light/dark cycle, and standard food and water were provided before the experiment. Mice received as little damage and pain as possible during all experiments.

The experimental instruments used included: laser confocal microscopy (Olympus, Melville, NY, USA), water maze (Panlab HARVARD, MA, USA), open field (Panlab HARVARD, MA, USA), mini vertical electrophoresis apparatus (BioRad Laboratories, Hercules, CA, USA), Bio-Rad fluorescence image analyzer (BioRad Laboratories, Hercules, CA, USA), cryomicrotome (Leica, Germany), and paraffin microtome (Leica, Germany).

Various antibodies were purchased from Millipore, Abcam, or Cell Signaling.

Aβ ELISA detection kit was purchased from Wuhan Elabscience Biotechnology Co., Ltd.

Experimental Method:
1. Mouse Administration Treatment

Gemfibrozil was administered to 8-month-old APP/PS1ΔE9 mice (male and female halves). Gemfibrozil was first dissolved in dimethyl sulfoxide (DMSO) at a concentration of 50 mg/mL, and then diluted to a final concentration of 50 μg/mL with mouse drinking water to obtain a drug solution. The mice in the administration group were allowed to freely drink the drug solution containing gemfibrozil, in which the final concentration of DMSO in the solution was 0.1%; and the mice in the control group were allowed to drink water containing 0.1% DMSO freely. All drinking devices contained with Gemfibrozil were wrapped in aluminum foil to prevent decomposition by exposure. During dosing, the drug solution was replaced every 2 days. Mice were measured daily for water consumption. After 2 months of dosing, all mice were subjected to behavioural experiments. Mice were placed in the laboratory to be behaviourally tested one hour prior to the start of daily behavioural studies, and all behavioural experiments were completed between 9 and 17 o'clock. All experiments involving animals were approved by Animal Ethics Committee of the Kunming Institute of Zoology, CAS.

2. The Spatial Learning and Memory Capacity of Mice by Water Maze Test

According to the application, a water maze experiment was adopted to evaluate the learning and memory capacity of AD mice after Gemfibrozil was administered for 2 months. The parameters of the used water maze were as follows: a circular pool having a diameter of 120 cm, a height of 50 cm, and a water depth of about 30 cm; and a cylindrical plastic lifesaving platform having a diameter of 10 cm, a height of 29 cm, and submerged 1 cm below the water surface. The water temperature was kept at 20+1° C. During the test, in order to prevent the mice from seeing the platform, white plastic foam was added to the water to spread on the water surface evenly until the lifesaving platform could not be seen, and the water was replaced every two days. The circular pool was divided into four quadrants, and the lifesaving platform was placed in the center of the third quadrant. A camera was arranged right above the water maze and used for recording the movement track of the mice. Mice were placed from the rearing room into a room for the water maze experiment for 1 hour before the start of each day of the experiment. The mice were trained for 7 consecutive days. The starting position was randomly changed among the four quadrants, the mice were allowed to explore freely for 1 minute, and the time required for the mice to find a lifesaving platform (also known as latency) was measured. If the mouse was able to find the platform within 1 minute, it was allowed to sit on the platform for 20 seconds, so that it can remember the location of the lifesaving platform based on surrounding markers. If the mouse failed to find the lifesaving platform in 1 minute, it would be carefully induced to reach the platform and allowed to stay for 20 seconds. Each mouse was trained at 90-minute intervals each day and randomly placed in the water maze in three different quadrants each day to look for the lifesaving platform. After 4 hours after the last training on the 7th day, the lifesaving platform of the water maze was removed. The mice were put into water, and the time, the distance and the speed of the mice around the lifesaving platform within 1 minute and the number of shuttles at the position of the lifesaving platform were measured, thereby evaluating the short-term memory capacity of the mice. After 72 hours after the last training on the 7th day, the lifesaving platform of the water maze was removed again. The mice were put into water, and the time, the distance and the speed of the mice around the lifesaving platform within 1 minute and the number of shuttles at the position of the lifesaving platform were measured, thereby evaluating the long-term memory capacity of the mice. During the experiment, the surrounding environment of the water maze should be kept consistent to avoid the influence of environmental factors. The behavior of the mice was followed and videotaped throughout the experiment using SMART 3.0 software (Panlab HARVARD, MA, USA). Behavioral parameters (speed, distance, time required to reach the lifesaving platform, percentage of time in each quadrant, percentage of distance in each quadrant) were automatically calculated by SMART 3.0 software based on the mouse behavior.

3. Detection of Anxiety Symptoms in Mice by Open Field Experiment

We evaluated the anxiety symptom behavior of APP/PS1ΔE9 mice 2 months after administration of Gemfibrozil using an open field experiment. APP/PS1ΔE9 mice following Gemfibrozil administration were selected as subjects and placed in an unfamiliar open field (40×40×40 inches) for 1 hour to record and track spontaneous motor activity and anxiety symptoms in the open field using SMART 3.0 software. The time lingering in the central region of the open field of the mouse is an important index for measuring anxiety symptoms of the mouse, and the smaller the time lingering in the central region of the open field of the mouse, the more obvious the anxiety symptoms of the mouse.

4. Expression of Related Proteins by Western Blot

The specific steps were as follows:

1) Extracting protein: the protein was extracted from the mouse brain tissue using western and an IP lysate from Beyotime Biotechnology.

2) Determining protein concentration: HM and U251-APP cells and mouse brain proteins were measured using a BCA protein quantification kit, and the extracted proteins were used for subsequent detection.

3) Pretreatment before loading: each sample was loaded at 20 μg depending on the protein concentration. The protein denaturant anhydrous mercaptoethanol was first added to denature the proteins at 95° C. for 6 minutes. After denaturation, the sample was placed on ice and stood for 5 minutes.

4) Loading and performing ectrophoresis: the denatured protein samples were loaded to the corresponding wells to start electrophoresis.

5) Membrane transfer treatment: according to the ratio of the reagent required by 1 L of a membrane transfer solution (10× membrane transfer solution: anhydrous methanol:water=1:2:7), a certain amount of the membrane transfer solution was prepared, the sponge and filter paper were immersed in the membrane transfer solution, and the PVDF membrane was previously immersed in anhydrous methanol for 30 seconds to be activated. A membrane transfer plate was manufactured according to the sequence of sponge-filter paper-glue-membrane-filter paper-sponge (the protein was negatively charged, and was transferred to a PVDF membrane towards the positive electrode). The membrane transfer plate was placed into a membrane transfer device, and the membrane transfer liquid was added to star the membrane transfer. The membrane transfer process needed to be carried out under an ice bath condition.

6) Blocking treatment: the protein-transferred PVDF membrane was placed in TBST containing 5% skimmed milk and placed on a shaker with slow shaking for 2 hours.

7) Primary antibody incubation: after blocking, the PVDF membrane was rinsed gently with TBST in order to wash off residual skimmed milk on the PVDF membrane. PVDF was cut according to the target protein molecular weight and the corresponding antibodies were added and incubated overnight on the shaker at 4° C.

8) Secondary antibody incubation: the next day, the primary antibodies were recovered and the PVDF membrane was rinsed with TBST three times, 5 min/time, to ensure that the remaining primary antibodies on the PVDF membrane were washed off. The corresponding secondary antibodies were then labeled according to the species origin of the primary antibodies (the secondary antibodies were formulated with 5% skimmed milk), and incubated for 1 hour at room temperature on the shaker.

9) Cleaning secondary antibody: the secondary antibodies were discarded and the PVDF membrane was rinsed with TBST three times, 5 min/time, to ensure that the remaining secondary antibodies on the PVDF membrane were completely washed off.

10) Developing: development was performed using a Bio-Rad fluorescence image analyzer to obtain the desired protein band of interest.

5. Immunofluorescence Staining of Mouse Brain Tissue

The main experimental steps were as follows:

1) Anesthetizing the mice: APP/PS1ΔE9 mice following Gemfibrozil administration were anesthetized systemically by intraperitoneal injection of pentobarbital (60 mg/kg).

2) Cardiac perfusion: after the mice were completely anesthetized, the abdominal cavity was cut with a scalpel to expose the cardiac tissue, which was perfused sequentially with 0.9% saline and 4% paraformaldehyde.

3) Tissue fixation: the mouse brain tissue was carefully removed and fixed in a 15 mL centrifuge tube containing 4% paraformaldehyde in an environment of 4° C. After 24 hours, 4% paraformaldehyde was replaced, the fixation was lasted for a total of 48 hours. The brain tissue was then dehydrated with 15% and 30% sucrose in PBS, respectively.

4) Embedding tissue and slicing: the dehydrated mouse brain tissue was embedded with an OCT embedding agent, and the hippocampus and cortex tissue were cut at a thickness of 10 μm/sheet using a cryomicrotome, collected on glass slides treated with polylysine, and stored in a −80° C. refrigerator for later use.

5) Antigen retrieval of tissue sections. The specific steps were as follows:

a. The frozen sections were removed from the refrigerator to return to room temperature, washed with PBS three times, 5 min/time, to remove the OCT embedding agent.

b. Citric acid antigen retrieval solution was diluted with PBS and the brain tissue was subjected to antigen retrieval.

c. Sections were washed with PBS three times, 5 min/time. The brain tissue sections were spin-dried and circled around the tissue with a Pap Pen.

6) Permeabilization treatment: 0.2% TritonX-100 was added dropwise to the sections, and allowed to stand at room temperature for 15 minutes to be permeabilized so as to ensure that subsequently incubated antibodies could be immersed in the cells.

7) Blocking: 5% BSA was blocked for 1 hour at room temperature.

8) First primary antibody incubation: the protein of interest primary antibodies, diluted with 2% BSA, were added dropwise, and incubated overnight at 4° C.

9) First secondary antibody incubation: the next day, the first primary antibodies were recovered. The first primary antibodies were washed with PBS three times, 5 min/time. The first secondary antibodies diluted in 2% BSA corresponding to the first primary antibodies were added dropwise to the sections and incubated for 1 hour at room temperature.

10) Second primary antibody incubation: sections were washed with PBS three times, 5 min/time. The second primary antibodies, diluted with 2% BSA, were added dropwise, and incubated overnight at 4° C.

11) Second secondary antibody incubation: on the third day, the second primary antibodies were recovered. The first antibodies were washed with PBS three times, 5 min/time. The second secondary antibodies diluted in 2% BSA corresponding to the second primary antibodies were added dropwise to the sections and incubated for 1 hour at room temperature.

12) Staining cell nucleus: the second secondary antibodies were discarded and the sections were washed with PBS three times, 5 min/time. DAPI was added dropwise to stain the nucleus and incubated at room temperature for 10 minutes.

13) Blocking: DAPI was discarded. The sections were washed with PBS three times, 5 min/time, and blocked with an anti-quenching agent.

14) Observations: the staining results were observed and acquired by a laser confocal microscope.

6. Immunohistochemical Staining of Mouse Brain Tissue

The main experimental steps were as follows:

1) Anesthetizing the mice: APP/PS1ΔE9 mice following Gemfibrozil administration were anesthetized systemically by intraperitoneal injection of pentobarbital (60 mg/kg).

2) Cardiac perfusion: the cardiac tissue was perfused sequentially with 0.9% saline and 4% paraformaldehyde.

3) Tissue fixation: the mouse brain tissue was removed and fixed in a 15 mL centrifuge tube containing 4% paraformaldehyde in an environment of 4° C. After 24 hours, 4% paraformaldehyde was replaced, the fixation was lasted for a total of 48 hours.

4) Tissue dehydration: the fixed brain tissue was dehydrated by using gradient ethanol, starting with a concentration of 50%, and then 75%, 80%, 95%, 100%, successively, that is, from low concentration to high concentration, so that the water in the brain tissue can be gradually replaced.

5) Tissue clearing: the brain tissue was cleared with xylene. The tissue was dehydrated and then transferred into xylene to be cleared, according to the tissue type, the tissue thickness, for about 30-90 minutes until the tissue was transparent.

6) Tissue wax-dipping: wax-dipping was performed with pure paraffin wax with slightly lower melting point in three-stage to remove xylene gradually from tissues.

7) Tissue embedding: during embedding, a preheated embedding box was taken, and spread with a layer of paraffin lightly. A tissue block was placed at room temperature when the paraffin was slightly coagulated, and the paraffin was poured until the tissue was completely immersed in the paraffin.

8) Paraffin slicing: it mainly included the following steps:

a. Slicing: the first thing to note is that the slicing knife is sharp and flat, which is critical to the quality of the sections.

b. The sliced wax section was initially spread firstly in water of normal temperature, and then placed in water of 45-48° ° C. to be fully spread, and finally adhered on a glass sheet. The sections were dried in a 37° C. oven.

9) Paraffin section dewaxing: the sections were put into xylene for dewaxing for 15 minutes, and the xylene was replaced twice; the sections were put into absolute ethyl alcohol for dewaxing for 5 minutes, the absolute ethyl alcohol was replaced and the operation was repeated; the sections were put into 85% ethanol for 5 minutes, and then 75% ethanol for 5 minutes, and finally washed with distilled water.

10) Antigen retrieval: tissue sections were subjected to antigen retrieval in a microwave oven in a retrieval box filled with EDTA antigen retrieval buffer (pH9.0), and heated with medium level for 8 minutes to boil. The heating was stopped for 8 minutes to keep warm, and then turned to a medium-low level for 7 minutes. After natural cooling the slides were washed three times in PBS (pH7.4) with shaking on a decolorizing shaker, 5 min/time.

11) Blocking endogenous peroxidases: sections were added into 3% hydrogen peroxide solution, and incubated for 25 minutes at room temperature in the dark. Then the slides were washed 3 times in PBS (pH 7.4) with shaking on the decolorizing shaker, 5 min/time.

12) Blocking serum: the tissue was evenly covered with 5% BSA dropwise in an immunohistochemistry circle and blocked for 30 minutes at room temperature.

13) Adding primary antibody: the blocking solution was gently decanted, the primary antibodies prepared in PBS were added dropwise to the sections, and the sections were incubated overnight in a humidified box at 4° C.

14) Secondary antibody incubation: the next day, the primary antibodies were recovered and the slides were washed 3 times in PBS (pH 7.4) with shaking on the decolorizing shaker, 5 min/time. After the sections were slightly spin-dried, the secondary antibodies (HRP-labeled) corresponding to the primary antibodies were dropped into the circle to cover the tissue, and incubated at room temperature for 1 hour.

15) DAB color development: the slides were washed 3 times in PBS (pH 7.4) with shaking on the decolorizing shaker, 5 min/time. After the sections were slightly spin-dried, the newly prepared DAB color developing solution was dropwise added into the circle, and the color developing time was controlled under the microscope. Brown-yellow indicates positive. The sections were washed with tap water to stop the color development.

17) Dehydrating and sealing: the sections were put sequentially into 75% ethanol for 5 minutes, 85% ethanol for 5 minutes, anhydrous ethanol for 5 minutes, wherein the absolute ethyl alcohol was replaced and the operation was repeated once, and xylene for 5 minutes to be dehydrated and cleared, the sections were removed from the xylene and air dried slightly, and sealed with neutral gum.

18) Microscopic examination (Pannoramic250/MIDI, 3DHISTECH) and image acquisition analysis.

7. Dendritic spine density in mouse brain neurons via Golgi staining

The FD Rapid GolgiStain™ Kit was used for dyeing, and the specific experimental steps were as follows:

1) Mixing solution A with solution B: at least the solution A and the solution B were mixed in equal volume gently and uniformly in advance, and the mixed solution was placed in a light-proof place at room temperature, wherein the required mixed solution was at least 5 times that of mouse brain tissue, and the dosage of each mouse was 5 mL.

2) Subpackaging the A-B mixed solution: the A-B mixed solution was dispensed into 15 mL centrifuge tubes in advance and protected from light.

3) Sampling of mouse brain tissues: the mice were anesthetized with pentobarbital (dosage of 60 mg/kg) to remove the brain, which was washed three times with purified water to clean off the bloodstains on the brains and then placed in the A-B mixed solution.

4) Replacing solution: after 24 hours, the A-B mixed solution was discarded and replaced with a new one, which was protected from light at room temperature for about two weeks.

5) After two weeks of staining in the A-B mixed solution, the brain tissue was transferred to 5 mL of solution C and stored in 4° C. After 24 hours, the solution was changed to a new solution C and left at 4° C. for about one week.

6) At the end of immersion in solution C, the mouse brain tissue was removed from solution C, dried with filter paper, then immediately frozen in liquid nitrogen, and sectioned with a cryomicrotome to a thickness of 100-150 μm.

7) The sections were aired at room temperature (attention is paid to keep away from light), for 3 days until the sections were dried, and subjected to subsequent dyeing.

a. Sections were washed 3 times with distilled water, 3 minutes/time.

b. Sections were put into a mixed solution of D and E for 10 minutes (the ratio of the components in the mixed solution was as follows: solution D:solution E:distilled water=1:1:2).

c. Sections were washed 3 times with distilled water, 5 min/time.

d. Sections were put sequentially into 75% ethanol for 5 minutes, 85% ethanol for 5 minutes, anhydrous ethanol for 5 minutes, wherein the absolute ethyl alcohol was replaced and the operation was repeated once, and xylene for 5 minutes to be dehydrated and cleared, the sections were removed from the xylene and air dried slightly, and sealed with neutral gum.

E. Microscopic examination. The staining results were observed by bright field microscopy.

8. Content of insoluble Aβ in mouse brain tissue by ELISA

The content of insoluble Aβ in brain tissue was detected by an ELISA kit (Elabscience), and the experiment was performed according to the instructions of the ELISA kit.

EXAMPLES

Example 1 Study of Gemfibrozil in Alleviating Symptoms of Cognitive Impairment in AD In order to study whether Gemfibrozil could alleviate the cognitive symptoms of AD, 8-month-old APP/PS1ΔE9 mice were selected for the water maze experiment after administration of gemfibrozil. Briefly, Gemfibrozil was dissolved in DMSO to 50 mg/ml and then diluted with mouse drinking water to a drug solution with a final concentration of 50 μg/mL, wherein the final concentration of DMSO in the drug solution was 0.1%. The mice were allowed to freely drink the drug solution. Control mice were allowed to freely drink water containing 0.1% DMSO. After continuous administration for two or two months, the APP/PS1ΔE9 mice in the gemfibrozil administration group and the control group were subjected to the water maze experiment to test the learning and memory capacity of mice in different groups. The results showed that all APP/PS1ΔE9 mice were able to find a lifesaving platform after 7 days of training. However, it can be seen that the learning ability of APP/PS1ΔE9 mice after administration of Gemfibrozil was significantly improved compared to the control group in that the escape time (A in FIG. 1, latency) and range (B in FIG. 1) required to reach the lifesaving platform were less than the control group. Notably, there was no difference in swimming speed between groups of mice (C in FIG. 1), indicating no difference in athletic ability between groups of mice.

Mice were tested for short-term memory capacity and long-term memory capacity 4 hours (D-F in FIG. 1) and 72 hours (G-I in FIG. 1) after the end of the last training, respectively. Compared with the control group, the short-term memory capacity of APP/PS1ΔE9 mice was significantly improved after administration of Gemfibrozil in that the lingering time (D in FIG. 1) and distance (E in FIG. 1) in the target quadrant after administration of Gemfibrozil in APP/PS1ΔE9 mice increase and that the number of shuttles at the position of the lifesaving platform (F in FIG. 1) increases. Consistent with this result, the long-term memory capacity of APP/PS1ΔE9 mice was significantly improved after administration of Gemfibrozil in that the lingering time (G in FIG. 1) and distance (H in FIG. 1) in the target quadrant after administration of Gemfibrozil in APP/PS1ΔE9 mice increase and that the number of shuttles at the position of the lifesaving platform (I in FIG. 1) increases.

Figure 1:
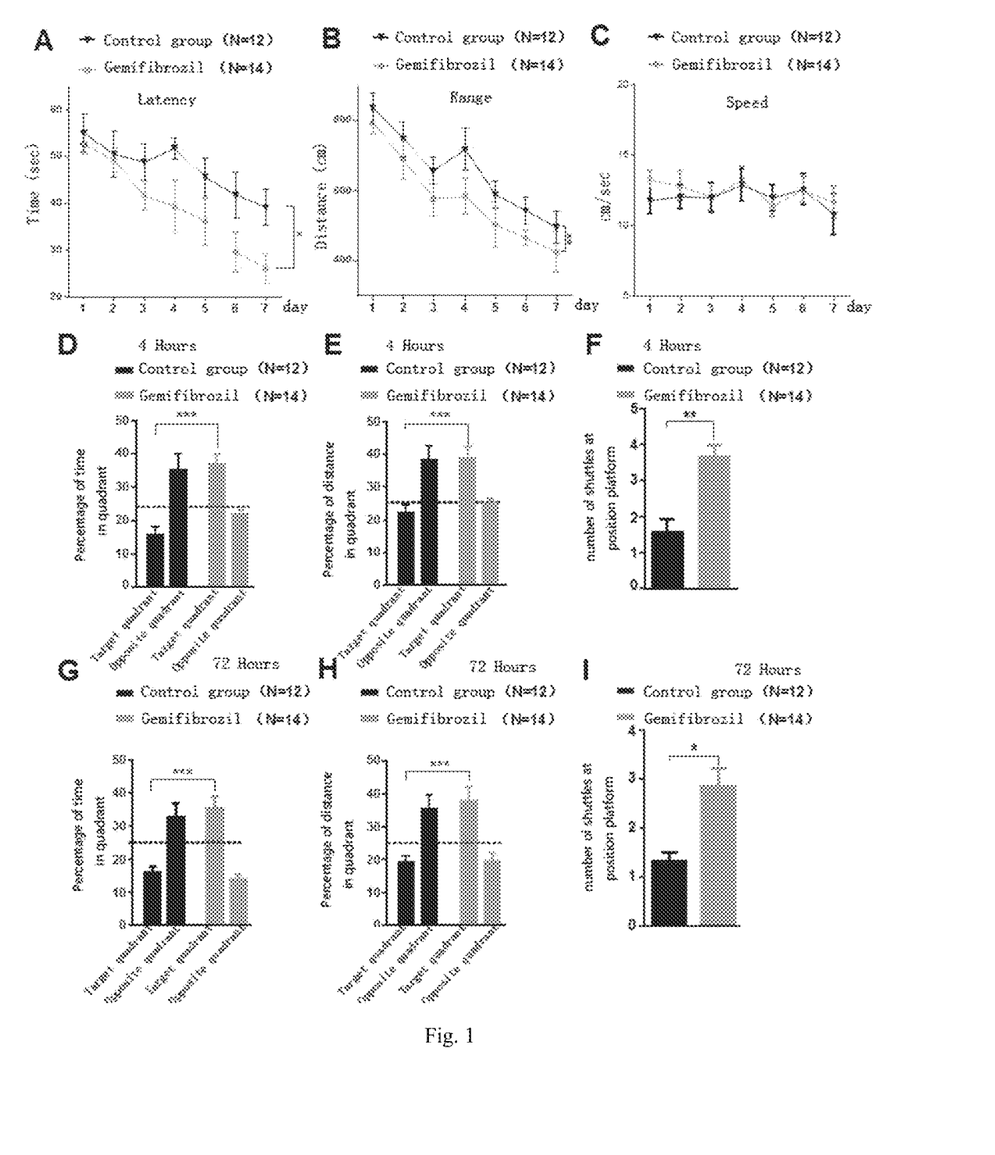
FIG. 1 shows that Gemfibrozil could improve cognitive dysfunction in APP/PS1ΔE9 mice.

From these results, it can be seen that Gemfibrozil can really improve cognitive impairment in APP/PS1ΔE9 mice.

Example 2 Study of Gemfibrozil in Alleviating Anxiety Symptoms in APP/PS1ΔE9 Mice Progressive cognitive decline and increased anxiety are two important clinical features of AD patients. To investigate whether Gemfibrozil could alleviate anxiety symptoms in APP/PS1ΔE9 mice, open field experiments were used for further testing. The results of the study showed no significant difference in athletic ability in APP/PS1ΔE9 mice with or without Gemfibrozil (A in FIG. 2 and B in FIG. 2). However, after administration of Gemfibrozil, the anxiety symptoms of APP/PS1ΔE9 mice were significantly alleviated; essentially, APP/PS1ΔE9 mice after administration of Gemfibrozil had significantly increased lingering time in the open field central region compared to the control group (A in FIG. 2 and C in FIG. 2).

Figure 2:
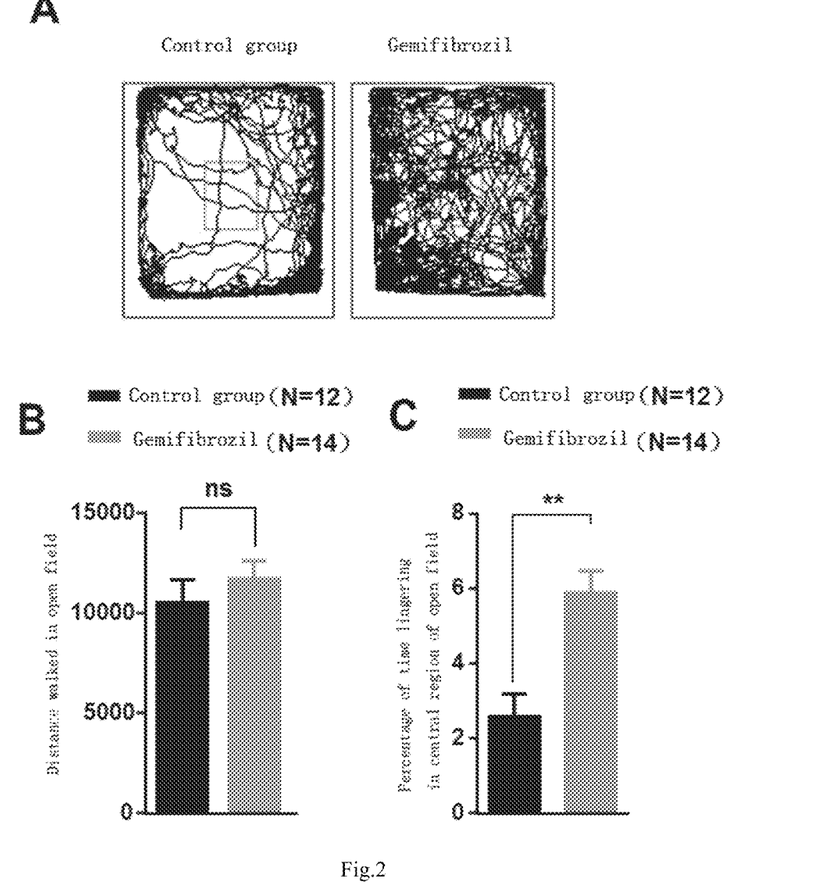
FIG. 2 shows that Gemfibrozil could alleviate anxiety symptoms in APP/PS1ΔE9 mice.

It can be seen that Gemfibrozil can indeed alleviate anxiety symptoms of AD mice.

Figure 3:
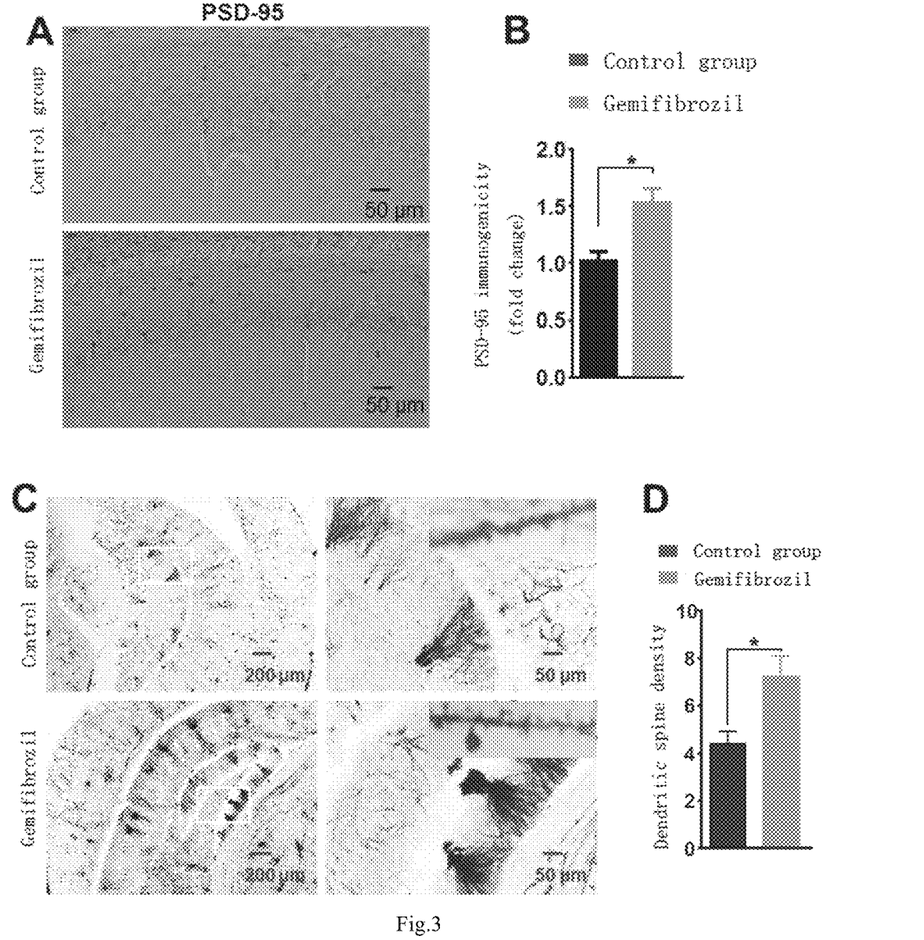
FIG. 3 shows that Gemfibrozil could improve neuroplasticity in APP/PS1ΔE9 mice.

Example 3 Study of Gemfibrozil in Improving Neuroplasticity in APP/PS1ΔE9 Mice In order to investigate whether Gemfibrozil could improve the neuroplasticity of APP/PS1ΔE9 mice, based on the improvement of cognitive dysfunction and anxiety in AD mice by Gemfibrozil, brain tissue samples were taken from AD mice treated with Gemfibrozil for 2 months, followed by immunohistochemistry and Golgi staining. Immunohistochemical results showed that the immunogenicity of PSD-95 protein was significantly up-regulated in the hippocampus of APP/PS1ΔE9 mice following Gemfibrozil administration (A-B in FIG. 3), suggesting that Gemfibrozil improves postsynaptic integrity in AD mice. Golgi staining results also showed that dendritic spine density was significantly up-regulated in hippocampal neurons of the APP/PS1ΔE9 mice following Gemfibrozil administration (C-D in FIG. 3).

In summary, Gemfibrozil can alleviate synaptic dysfunction and anxiety symptoms and improve cognitive impairment in APP/PS1ΔE9 mice.

Example 4 Study of Gemfibrozil in Attenuating Pathological Features of AD

Figure 4:
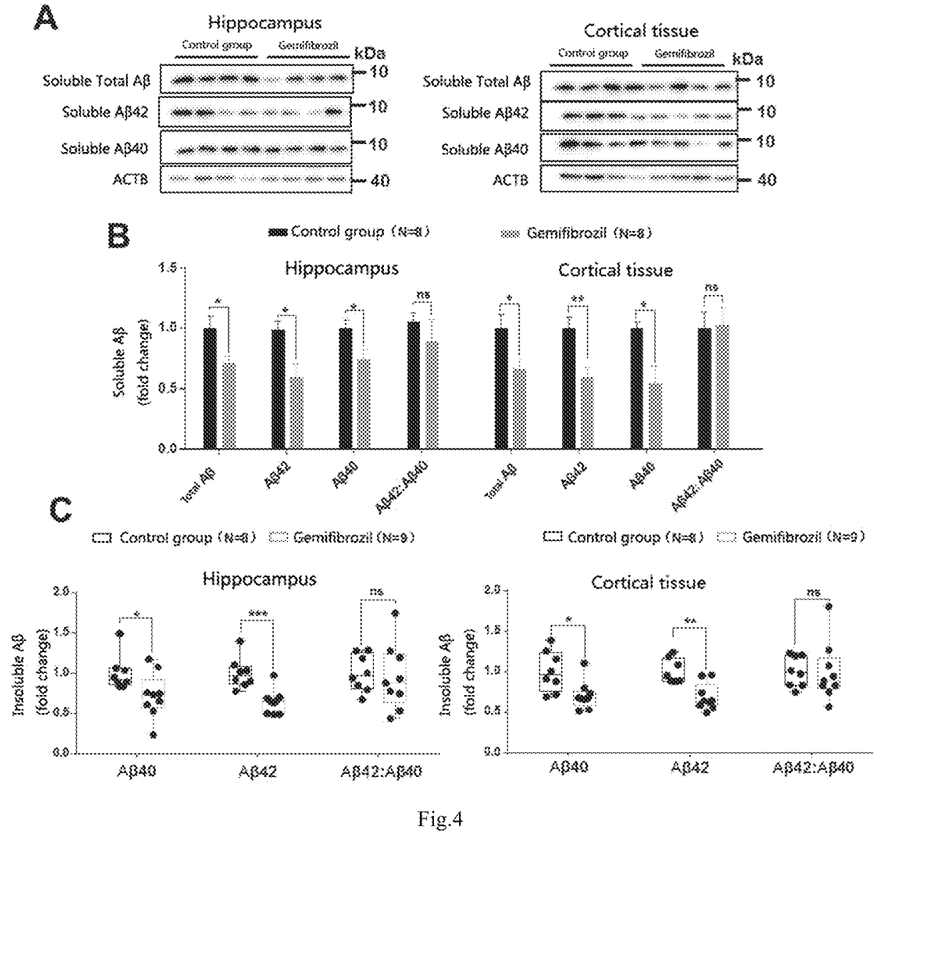
FIG. 4 shows that Gemfibrozil could reduce the pathological characteristics of soluble and insoluble Aβ in AD mice.
Figure 5:
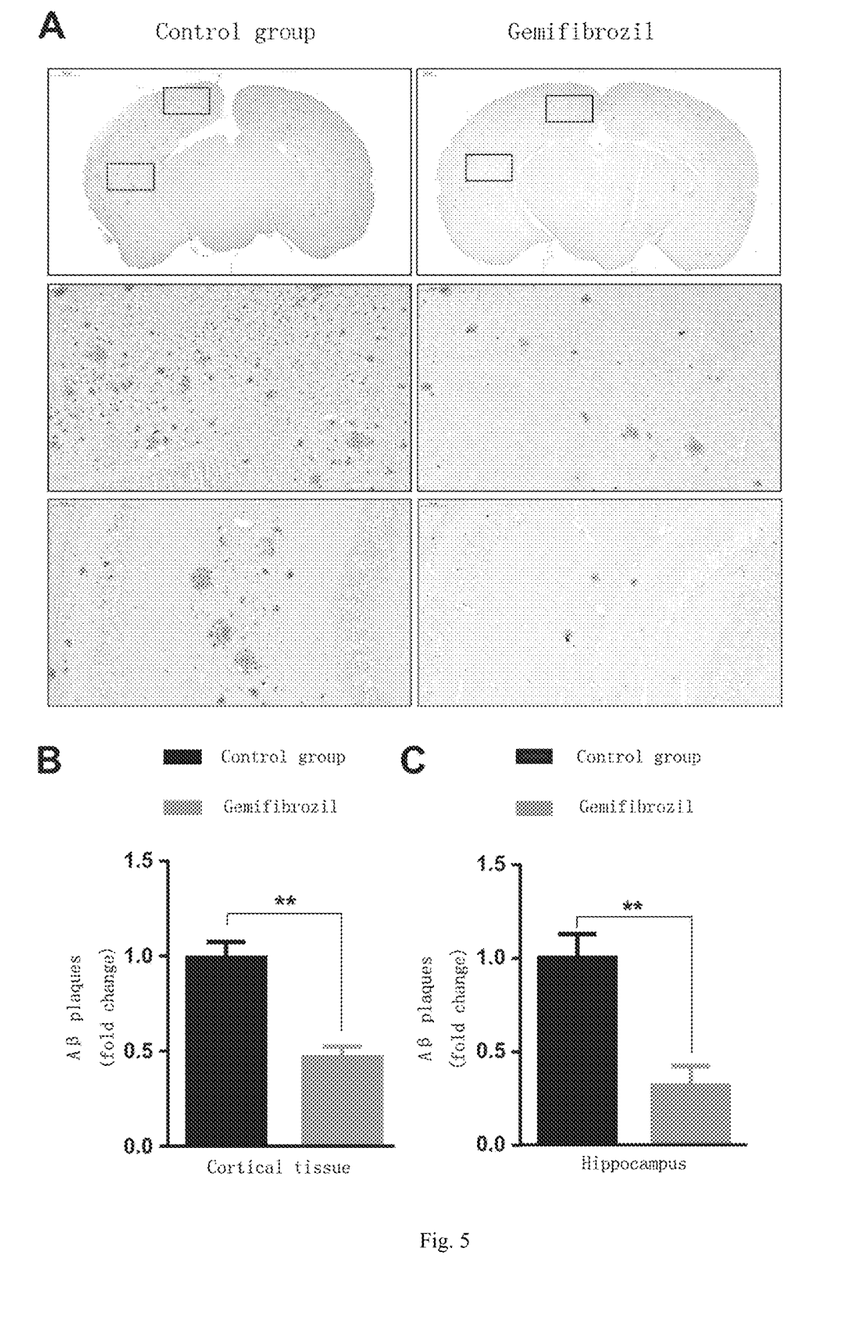
FIG. 5 shows that Aβ plaque deposition in the brain tissue of an APP/PS1ΔE9 mouse is significantly reduced after administration of gemfibrozil.

To further explore whether Gemfibrozil could alleviate the pathological features of AD, Aβ in brain tissues of APP/PS1ΔE9 mice administered or not with Gemfibrozil were examined. Western blot results showed that soluble Aβ was significantly reduced in the hippocampus and cortex of APP/PS1ΔE9 mice after administration of Gemfibrozil compared to the control group (A-B in FIG. 4). Notably, the levels of Aβ42 and Aβ40, which play an important neurotoxic role, decreased significantly after administration of Gemfibrozil, although the ratio of the two did not change significantly between groups (A-B in FIG. 4). Further using ELISA detection, it was found that the ratio of insoluble Aβ42 and Aβ40 in hippocampus and cortex tissues of APP/PSIAE9 mice after administration of gemfibrozil did not change significantly, but the amount of both are significantly reduced (C in FIG. 4), compared to the control group. Immunohistochemical staining results further showed that the deposition of Aβ plaques labeled with Aβ (4G8) antibodies in the brain tissue of the APP/PS1ΔE9 mouse after administration of Gemfibrozil was significantly reduced compared to the control group (A-C in FIG. 5).

It can be seen that Gemfibrozil can improve Aβ pathology in APP/PS1ΔE9 mice.

Example 5 Study of Gemfibrozil in Activating Astrocytes and Microglia to Alleviate the Pathological Features of Aβ

Based on previous scientific findings, astrocytes surround Aβ plaques, encapsulate and degrade intracellular Aβ in the brain tissue of AD patient. In addition, activated microglia also aggregate around Aβ plaques in the brain tissue of the AD patient, limiting the formation of Aβ plaques by phagocytosis of Aβ. Early pathological progression of AD manifests as dysfunction of glial cells, which in turn leads to inadequate clearance of Aβ, thereby causing synaptic dysfunction.

Figure 6:
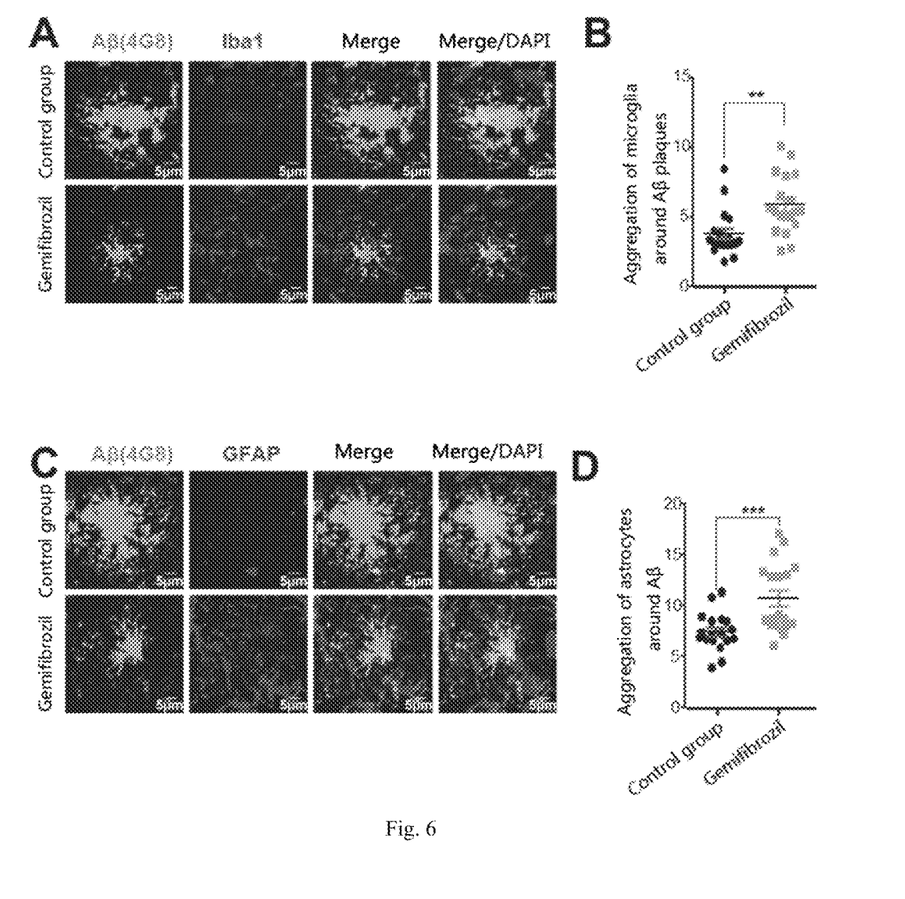
FIG. 6 shows that administration of Gemfibrozil induces the aggregation of microglia and astrocytes in the brains of APP/PS1ΔE9 mice around Aβ plaques.

To investigate whether Gemfibrozil could activate astrocytes and microglia to alleviate the pathological features of Aβ, immunofluorescence was performed on brain tissues of APP/PS1ΔE9 mice administered or not with Gemfibrozil. Compared with control APP/PS1ΔE9 mice, the degree of co-localization of the marker Iba1 for microglia with Aβ plaques (A-B in FIG. 6) and the degree of co-localization of GFAP for astrocytes with Aβ plaques (C-D in FIG. 6) in brain tissue of APP/PS1ΔE9 mice administered Gemfibrozil was significantly increased. This suggests that Gemfibrozil can activate the aggregation of astrocytes and microglia towards Aβ plaques and clears them.

Therefore, Gemfibrozil can relieve pathological features of AD by activating astrocytes and microglia so as to improve neuroplasticity, and finally achieve the effects of alleviating and treating AD.

The foregoing is only a preferred embodiment of the present application and is not intended to limit the scope of the present application. Any modification, equivalent replacement, improvement, etc., made within the spirit and principle of the present application shall be included in the scope of the present application.

The invention claimed is:

1. A pharmaceutical composition for treating and/or preventing a neurodegenerative disease, wherein the pharmaceutical composition comprises Gemifibrozil, or a pharmaceutically acceptable salt, ester, or stereoisomer thereof,
   wherein the pharmaceutical composition further comprises a second therapeutically active agent, the second therapeutically active agent is memantine hydrochloride and/or sodium oligomannate, and
   wherein the pharmaceutical composition further comprises one or a plurality of pharmaceutically acceptable carriers.

2. The pharmaceutical composition of claim 1, wherein Gemfibrozil, or the pharmaceutically acceptable salt, ester, or stereoisomer thereof is present in a content of 1-99% based on the total weight of the pharmaceutical composition.

3. A method for treating and/or preventing a neurodegenerative disease, comprising administering a pharmaceutical composition comprising Gemifibrozil, or a pharmaceutically acceptable salt, ester, or stereoisomer thereof to a subject in need thereof,
wherein the pharmaceutical composition further comprises a second therapeutically active agent, the second therapeutically active agent is memantine hydrochloride and/or sodium oligomannate, and
wherein the pharmaceutical composition further comprises one or more pharmaceutical carriers.

4. The method of claim 3, wherein a daily dosage of the pharmaceutical composition administered to the subject in need thereof is 0.1-100 mg/kg body weight based on Gemfibrozil, or the pharmaceutically acceptable salt, ester, or stereoisomer thereof.

5. The pharmaceutical composition of claim 1, wherein Gemfibrozil, or the pharmaceutically acceptable salt, ester, or stereoisomer thereof is present in a content of 20-80%, based on a total weight of the pharmaceutical composition.

6. The pharmaceutical composition of claim 1, wherein Gemfibrozil, or the pharmaceutically acceptable salt, ester, or stereoisomer thereof is present in a content of 40-60%, based on a total weight of the pharmaceutical composition.

7. The method of claim 3, wherein a daily dosage of the pharmaceutical composition administered to a subject in need thereof is 0.5-20 mg/kg body weight based on Gemfibrozil, or the pharmaceutically acceptable salt, ester, or stereoisomer thereof.

* * * * *

UNITED STATES PATENT AND TRADEMARK OFFICE
CERTIFICATE OF CORRECTION

| | | |
|---|---|---|
| PATENT NO. | : 12,048,680 B2 | Page 1 of 1 |
| APPLICATION NO. | : 17/278994 | |
| DATED | : July 30, 2024 | |
| INVENTOR(S) | : Yonggang Yao | |

It is certified that error appears in the above-identified patent and that said Letters Patent is hereby corrected as shown below:

In the Specification

Column 2, Line 61, change "Gemifibrozil" to --Gemfibrozil--.
Column 2, Lines 65-66, change "Gemifibrozil" to --Gemfibrozil--.
Column 3, Lines 14-15, change "Gemifibrozil" to --Gemfibrozil--.
Column 3, Lines 20-21, change "Gemifibrozil" to --Gemfibrozil--.
Column 3, Line 41, change "Gemifibrozil" to --Gemfibrozil--.
Column 9, Line 51, change "Gemifibrozil" to --Gemfibrozil--.
Column 9, Line 55, change "Gemifibrozil" to --Gemfibrozil--.
Column 12, Line 44, change "ectrophoresis" to --electrophoresis--.
Column 18, Line 59, change "Gemifibrozil" to --Gemfibrozil--.
Column 19, Line 7, change "Gemifibrozil" to --Gemfibrozil--.

Signed and Sealed this
Eleventh Day of February, 2025

Coke Morgan Stewart
*Acting Director of the United States Patent and Trademark Office*